United States Patent
Erickson (10) Patent No.: US 11,243,280 B2
(45) Date of Patent: Feb. 8, 2022

(54) AUGMENTED TUNE/MATCH CIRCUITS FOR HIGH PERFORMANCE DUAL NUCLEAR TRANSMISSION LINE RESONATORS

(71) Applicant: University of Florida Research Foundation, Inc., Gainesville, FL (US)

(72) Inventor: Matthew G. Erickson, Gainesville, GA (US)

(73) Assignee: University Of Florida Research Foundation, Inc., Gainesville, FL (US)

(*) Notice: Subject to any disclaimer, the term of this patent is extended or adjusted under 35 U.S.C. 154(b) by 32 days.

(21) Appl. No.: 16/486,777

(22) PCT Filed: Feb. 20, 2018

(86) PCT No.: PCT/US2018/018754
§ 371 (c)(1),
(2) Date: Aug. 16, 2019

(87) PCT Pub. No.: WO2018/152511
PCT Pub. Date: Aug. 23, 2018

(65) Prior Publication Data
US 2019/0369178 A1    Dec. 5, 2019

Related U.S. Application Data

(60) Provisional application No. 62/461,108, filed on Feb. 20, 2017.

(51) Int. Cl.
*G01R 33/36*    (2006.01)
*G01R 33/341*   (2006.01)
(Continued)

(52) U.S. Cl.
CPC ....... *G01R 33/3635* (2013.01); *G01R 33/341* (2013.01); *G01R 33/345* (2013.01); *G01R 33/3685* (2013.01); *A61B 5/055* (2013.01)

(58) Field of Classification Search
CPC ............. A61B 5/055; G01R 33/34092; G01R 33/341; G01R 33/345; G01R 33/3635; G01R 33/3685
See application file for complete search history.

(56) References Cited

U.S. PATENT DOCUMENTS 5,107,217 A * 4/1992 Duerr ................. G01R 33/3635
                                                  324/322
5,355,087 A * 10/1994 Claiborne ............ A61B 5/4381
                                                  324/322
(Continued)

OTHER PUBLICATIONS

International Search Report dated May 4, 2018.
(Continued)

*Primary Examiner* — Steven L Yeninas
(74) *Attorney, Agent, or Firm* — Thomas | Horstemeyer, LLP (57) ABSTRACT

A dual nuclear MR transmission line resonator is capable of operating on $^1$X pairs, with X being $^{31}$P, $^{23}$Na, $^3$He, or $^{129}$Xe. The resonator avoids many of the problems inherent in conventional dual nuclear designs. No LC trap is used, and the coil has substantially the same spatial profile on both nuclei. In the resonator, an augmented MR tune/match circuit, includes a conventional capacitive L circuit, with the L circuit shunted at a match point by a notch filter tuned to a frequency of a companion nucleus. Also disclosed is a method for simultaneously resonating conductive loops of surface coils or conductive elements of volume coils simultaneously on both $^1$H and X with hybrid transmission line termination elements bonded to the resonator loop or conductive elements in shunt with respect to one another.

15 Claims, 10 Drawing Sheets

(51) Int. Cl.
  *G01R 33/345* (2006.01)
  *A61B 5/055* (2006.01)

(56) References Cited

U.S. PATENT DOCUMENTS

| | | | |
|---|---|---|---|
| 6,104,943 A | 8/2000 | Frederick et al. | |
| 6,313,631 B1* | 11/2001 | Fiat | G01R 33/3635 324/307 |
| 6,424,234 B1* | 7/2002 | Stevenson | A61N 1/3752 333/182 |
| 7,872,476 B2* | 1/2011 | Ikeda | G01R 33/3635 324/322 |
| 10,761,159 B2* | 9/2020 | Jones | G01R 33/3657 |
| 2004/0239324 A1 | 12/2004 | Hardy et al. | |
| 2007/0279061 A1 | 6/2007 | Erickson et al. | |
| 2009/0118611 A1* | 5/2009 | He | G01R 33/3635 600/422 |
| 2010/0253333 A1* | 10/2010 | Zhai | G01R 33/3635 324/307 |
| 2012/0112748 A1* | 5/2012 | Hetherington | G01R 33/3635 324/318 |
| 2013/0271141 A1* | 10/2013 | Zhang | G01R 33/34092 324/318 |
| 2013/0289666 A1* | 10/2013 | Johnson | A61B 5/7203 607/63 |
| 2017/0085113 A1* | 3/2017 | Yang | H02J 7/025 |
| 2018/0210045 A1* | 7/2018 | Guan | G01R 33/3621 |
| 2019/0089210 A1* | 3/2019 | Weale | H04B 5/0037 |

OTHER PUBLICATIONS

Erickson et al. TEM Transmission Line Coil with Double Nuclear Capability. Magnetic Resonance in Medicine 58: 800-807, 2007. [retrieved on Apr. 15, 2018], Retrieved from Internet. <URL:https://onlinelibrary.wiley.com/doi/pdf/10.1002/mrm.21394>.

* cited by examiner

AUGMENTED TUNE/MATCH CIRCUITS FOR HIGH PERFORMANCE DUAL NUCLEAR TRANSMISSION LINE RESONATORS

CROSS-REFERENCE TO RELATED APPLICATION

This application is the 35 U.S.C. § 371 national stage application of PCT Application No. PCT/US2018/018754, filed Feb. 20, 2018, which claims priority to, and the benefit of, U.S. Provisional Application No. 62/461,108, filed Feb. 20, 2017.

FIELD OF THE DISCLOSURE

The disclosure relates to augmented tune/match circuits for high performance dual nuclear transmission line resonators.

BACKGROUND

NMR/MRI "coils" are radio frequency devices designed to 1) Produce a radio frequency magnetic field at the resonance frequency, or Larmor frequency co, of active nuclei such as $^1$H, $^{13}$C, $^{19}$F, $^{31}$P, $^3$He, $^{23}$Na, and $^{129}$Xe (List not exhaustive), thereby enabling the "tipping" of nuclear spin from one state to the other, and 2) act as receive antennas for the radio signal emitted by tipped nuclei whilst returning to their lower nuclear spin state. Many coil designs have been described over the years. Coils may be linearly polarized or circularly polarized. Both volume coils and surface coils are employed in practice. Volume coils view a relatively large spatial volume, while surface coils are used to examine relatively small regions of interest.

The past 15 years have witnessed the development of NMR/MR hyperpolarization techniques, in which NMR active nuclei are prepared in a nonthermal or nonequilibrium state, such that nuclei in the high energy spin state grossly outnumber nuclei in the low energy spin state, allowing for a transient but spectacular increase in MR signal intensity. Nuclei successfully hyperpolarized to date include $^3$He, $^{13}$C, and $^{129}$Xe. Of these, $^{13}$C is probably the most important, given that metabolically active carbon compounds such as pyruvate, alpha-ketoglutarate, and alanine may be labeled with $^{13}$C and hyperpolarized. These hyperpolarized reagents may be introduced into living organisms, with their subsequent metabolism being monitored by MR imaging or spectroscopy. Hyperpolarized reagents yield 10,000 to 25,000 times more signal than an equal quantity of thermal reagent. For example, $^{13}$C pyruvate may be injected, and the subsequent evolution of lactate and bicarbonate signals may be tracked along with the pyruvate. Such compounds have great potential as noninvasive metabolic markers for the probing of heart disease and malignancies. The sensitivity of hyperpolarized 13C metabolic imaging probes is good, and the technique does not saddle subjects with accrued ionizing radiation exposure, as does PET scanning. In order to best exploit hyperpolarized reagents, good dual nuclear MR coils are required. The ideal coil would be a dual tuned coil capable of operating at high efficiency on both $^1$H and $^{13}$C, all while maintaining a similar profile on each nucleus.

As is known in the field (and used herein), efficiency is defined as follows. Real coils are compared to a hypothetical ideal (lossless) coil, so we have the concept of $SNR_{real}$/$SNR_{perfect}$, where SNR means signal to noise ratio. This expression is given by: $SNR_{real}/SNR_{perfect} = (1-Q_L/Q_U)^{1/2}$ where $Q_L$ is the Loaded Quality Factor and $Q_U$ is the Unloaded Quality Factor. If the Q ratio is 3, there is an efficiency of about 81%. Accordingly, a $Q_L/Q_U$ ratio of around 3 or more is considered in the field as a high efficiency or high performance coil.

Most dual resonant coil designs to date involve modifying surface coils or birdcage coils with lossy LC trap circuits. This is understandable, for these two designs have served as "work horses" for many decades. In addition to degrading coil efficiency on at least one frequency, trapping these coils may also introduce $B_1$ field uniformity issues. Dual nuclear TEM type coils have been described (1994), but in many cases the dual nuclear efficiency has not been rigorously quantified.

Recently, CMDM coils have been described, along with volumes coil constructed from microstripline elements, with alternating elements resonated on either $^1$H or $^{13}$C. In 2007, a group described a volume coil in the TEM family. Again, resonance of conductive rungs alternated between $^1$H and X frequencies.

An "ideal" dual nuclear coil would function with high efficiency on both $^1$H and X. It would have identical or near identical spatial profiles on each, and would dispense with lossy devices such as LC traps. This ideal holds for all dual nuclear $^1$H/X coils, and not just those designed with hyperpolarized agents in mind. For example, there is considerable interest in clinical applications of $^1$H/$^{23}$Na in CNS work. Ideally, a good $^1$H/X coil would also have a high degree of port to port isolation between $^1$H and X tune/match circuits. To date, such a coil has remained elusive.

SUMMARY OF THE DISCLOSURE

This disclosure describes a $^1$H/X coil with several distinct advantages. The design may be used over a wide range of field strengths, and may be applied to virtually any $^1$H/X combination, with possible exception of $^1$H/$^{19}$F. Advantages include the following: 1) No lossy LC trap is used in the design. 2) No lumped constant is used in the active region of the coil; capacitance and inductance are uniformly distributed. 3) The active elements of the coil are simultaneously resonated on both $^1$H and X with high efficiency. This ensures that the resonator has the same spatial profile on both $^1$H and X. 4) Isolation between the $^1$H port and X port is outstanding, typically 45 dB or better. As a result, the two resonators tune and match smoothly, with virtually no dynamic interaction between the two. In fact, simultaneous operation on $^1$H and X is feasible given proper pulse control software and T/R console electronics.

This disclosure is applicable to both surface coils and volume coils. It is a transmission line resonator. In coils of this type, current anti-nodes, or virtual grounds are established by taking advantage of properties inherent to transmission lines, specifically ¼ wave lines, or hybrid lines, composed of a transmission line terminated on one end by a capacitor. Transmission line resonators have the advantage of high Q at VHF and UHF frequencies, along with the advantage of uniformly distributed capacitance along the conductors in the active region of the coil. The active region of the coil is the region where specimens are placed for MR imaging or spectroscopy. In volume coils, the active region may be referred to as the utility volume.

In an embodiment, a dual nuclear MR transmission line resonator is capable of operating on $^1$H/X pairs, wherein X is $^{31}$P, $^{23}$Na, $^3$He, or $^{129}$Xe. The conductive elements in a utility region of the resonator are simultaneously resonated on both $^1$H and X with high efficiency.

Both the $^1$H and X resonator can have virtually identical spatial distributions, as both the $^1$H and X resonator use the same active elements. Both the $^1$H and X resonator can operate substantially independently of each other such that each may act as an independent T/R coil, either alone, or in synchrony with the other resonator of the $^1$H/X pair.

In another embodiment, a resonator in which a $B_0$ static field of a MR magnet may be fine adjusted with a $^1$H member of a $^1$H/X pair, automatically provides the same information for a X member of the pair, as both resonators have perfect spatial co-registry with respect to each other.

The disclosure also relates to a method for simultaneously resonating conductive loops of surface coils, or conductive elements of volume coils simultaneously on both 1H and X with a plurality of hybrid transmission line termination elements, with the elements bonded to the resonator loop or conductive elements in shunt with respect to one another.

In another embodiment, an augmented MR tune/match circuit comprises a conventional capacitive L circuit, with the L circuit shunted at a match point by a notch filter tuned to a frequency of a companion nucleus.

The notch filter can be constructed from a hybrid transmission line circuit or a helical resonator notching at the companion nucleus frequency. The augmented tune/match circuit can act as a normal tune/match port at a design frequency, while acting as a pure capacitive termination at the frequency of the companion nucleus. In some embodiments, the switching between these two actions is passive and automatic.

A plurality of resonators using the circuits can be configureable in arrays suitable for an accelerated imaging modality, such as SMASH (SiMultaneous Acquisition of Spatial Harmonics) or SENSE (SENSitivity Encoding).

One or a plurality of resonators may be run off conventional analog T/R circuitry such as quadrature hybrids, or may be used in conjunction with at least one of multi-channel DDS controlled transmitters and multi-channel digital receivers.

Other objectives and advantages of this disclosure will become apparent from the following description taken in conjunction with the accompanying drawings, wherein are set forth, by way of illustration and example, certain embodiments of this disclosure. The drawings constitute a part of this specification and include exemplary embodiments of the present disclosure and illustrate various objects and features thereof.

BRIEF DESCRIPTION OF THE DRAWINGS

A more complete understanding of the present disclosure may be obtained by references to the accompanying drawings when considered in conjunction with the subsequent detailed description. The embodiments illustrated in the drawings are intended only to exemplify the disclosure and should not be construed as limiting the disclosure to the illustrated embodiments.

In all of the above-identified Figures illustrating schematic diagrams (FIGS. 1A, 1B, 2, and 5-8), it should be noted that there are no mechanical switches as the switch schematic symbols are used to indicate the selective wave interference (filtering) effects at both $^1$H and X.

DETAILED DESCRIPTION

As required, embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

The device described in this disclosure is a dual nuclear MR resonator suitable for both imaging and spectroscopy. Specifically, it is designed to operate simultaneously on the MR resonance frequency of proton and one additional nucleus, designated generically as X. In practice, X may be $^{13}$C, $^{23}$Na, $^3$He, $^{129}$Xe, or $^{31}$P. $^{19}$F may be problematic because its frequency is very close to $^1$H. $^3$He may demand the use of helical resonator notch filters in lieu of transmission line hybrid filters, as will be discussed later.

In the disclosed device, a plurality of hybrid transmission line notch filters and line terminators serves to effect a virtual short, or virtual ground in the center of a conductive loop in the case of a surface coil, or in the center of both members of a conjugate pair of conductive elements in a volume coil on both $^1$H and X frequencies. The term conjugate pair refers to the amplitude and phase relationship between members of the pair. Each member carries equal RF current at each frequency, but with a phase difference of 180 degrees between the two members of the pair. The virtual ground is a point of high conductance or low resistance. When RF power is applied, large RF currents are generated, thereby generating the required RF magnetic field ($B_1$ field) for MR experiments.

In the disclosed device, the same plurality of hybrid transmission notch filters and termination elements also serves to isolate the RF energy at the $^1H$ frequency from the X tune/match port, while simultaneously isolating RF energy at the X nucleus frequency from the $^1H$ tune/match port.

A key to the operation of the disclosed device is that hybrid transmission line termination elements and hybrid transmission line notch filters may be configured to serve as high efficiency, frequency dependent passive switches. No MEMS device, PIN diode, or other active element is required. The line insertion loss of the hybrid notch filters is very low, typically 0.05 dB or less. At the same time, isolation between the $^1H$ tune/match port and the X tune/match port is very high, typically exceeding −45 dB. Both the $^1H$ and X resonance tune and match virtually independent of each other, and unloaded Q (quality factor) is high on both.

Figure 5:
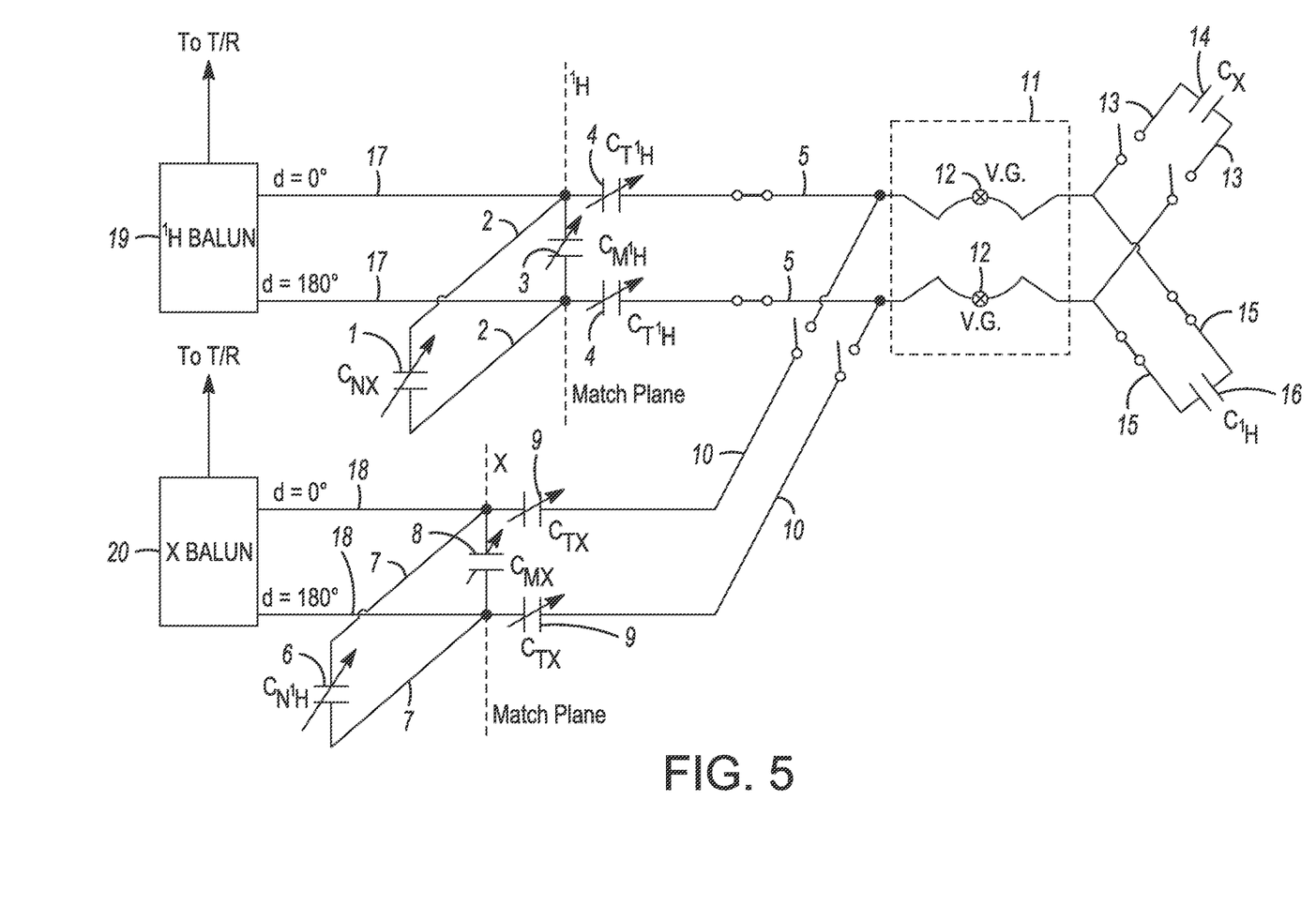
FIG. 5 is a schematic diagram illustrating $^1$H nucleus frequency T/R behavior.
Figure 6:
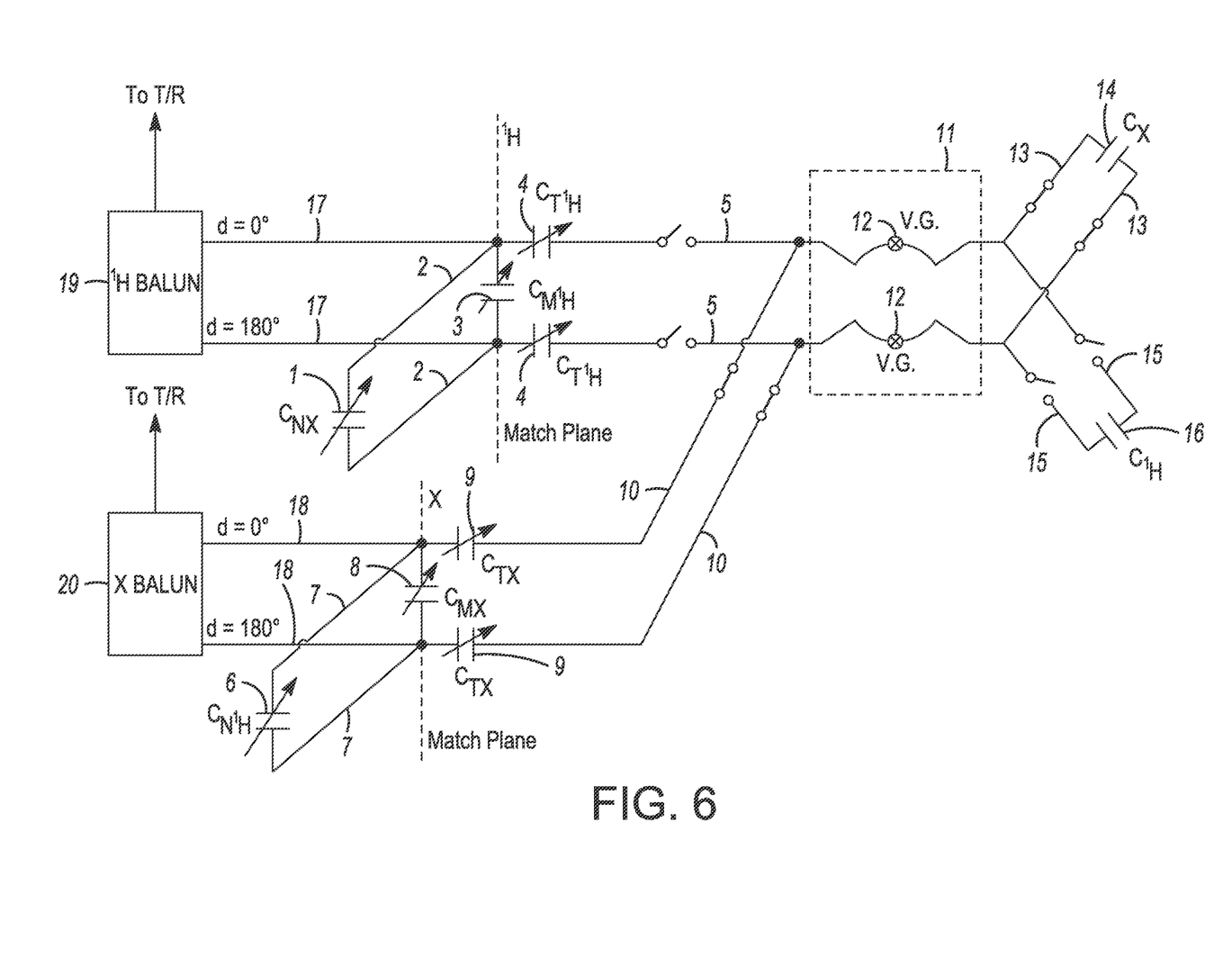
FIG. 6 is a schematic diagram illustrating X nucleus frequency T/R behavior.
Figure 7:
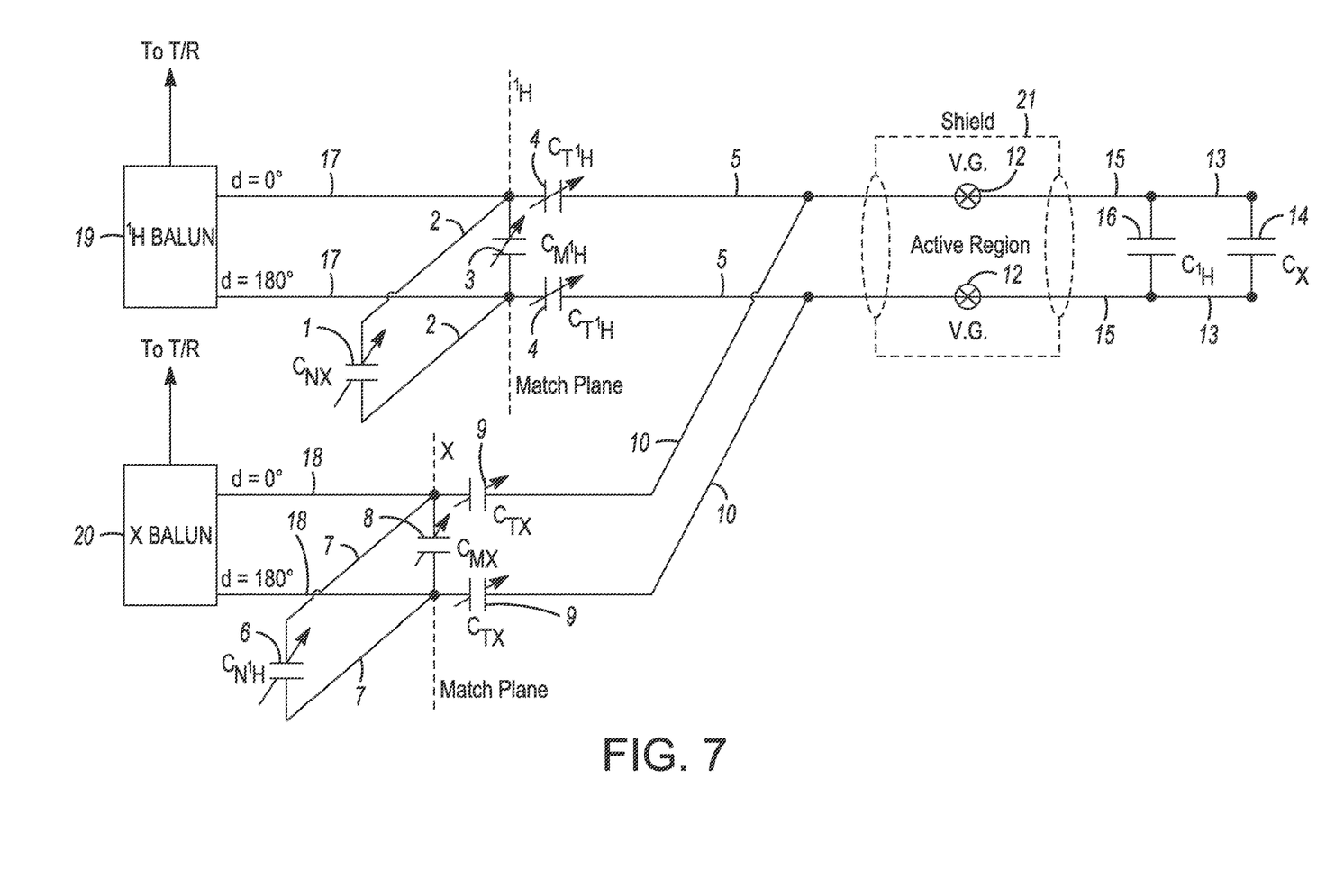
FIG. 7 is a schematic diagram illustrating a volume coil driven pair electrical circuit according to an embodiment of the disclosure.
Figure 8:
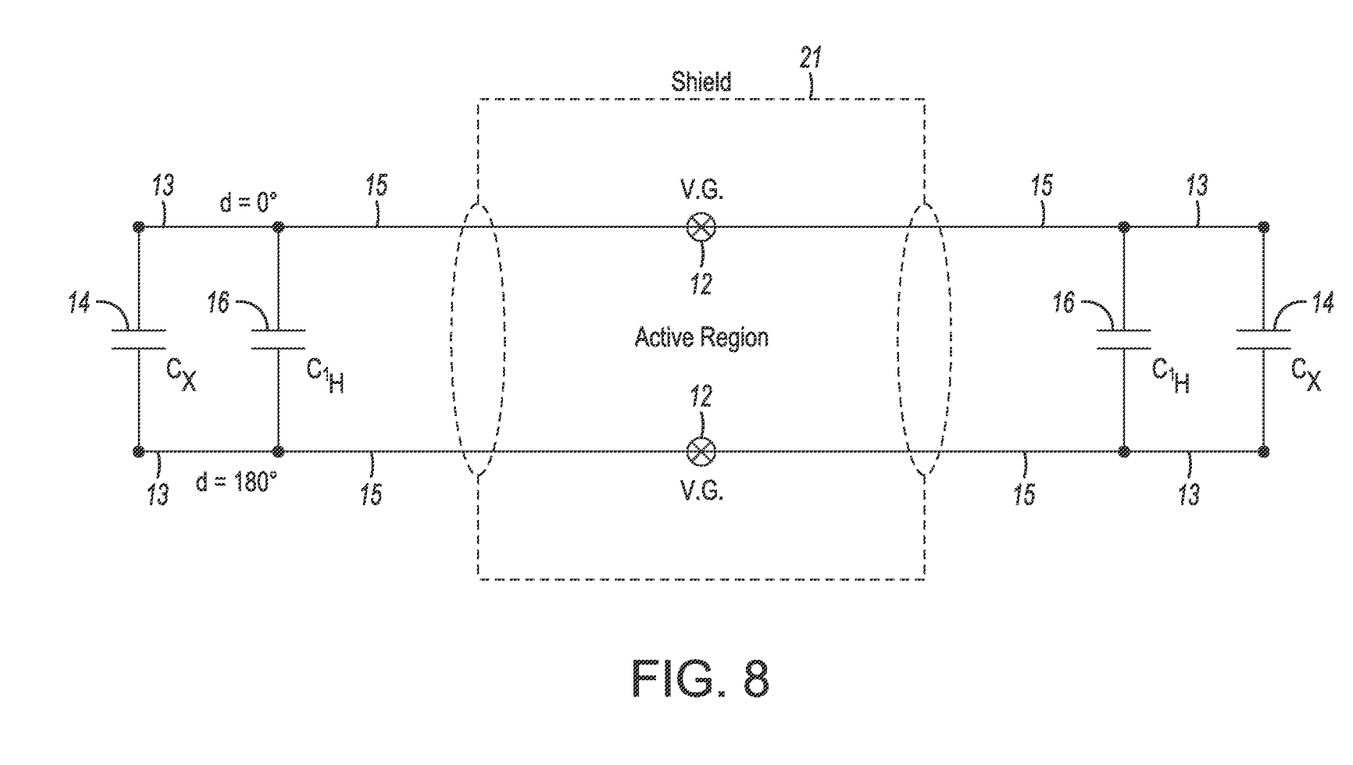
FIG. 8 is a schematic diagram illustrating a volume coil passive pair electrical circuit according to an embodiment of the disclosure.

A conceptual schematic of the resonator design according to the disclosure is shown in FIGS. 5 and 6. Though a surface coil loop is shown in FIGS. 5 and 6, the same operation applies to volume coils based on the disclosed design as shown in FIGS. 7 and 8.

Technical Description And Operation

The coil design disclosed herein is a type of transmission line resonator. Coils of this design exploit the fact that open circuit quarter wave lines give near short circuits (low resistance) on the opposite end, while short circuited quarter wave lines give near open circuits, or high resistances on the opposite end. All things being equal, the unloaded Q of a transmission line resonator increases with operating frequency. These devices typically perform well at VHF frequencies and above. In MR work, this usually means 30 MHz or above.

The transmission line resonator approach may be improved by terminating a section of transmission line of some length less that $\lambda/4$ with a capacitor. The reactance of the capacitor is chosen to cancel the short circuit reactance (inductive) of the line segment at the desired operating frequency. Such a device is called a hybrid transmission line stub. In preferred embodiments, capacitors are used rather than inductors, given the inherent losses associated with the latter.

At any given frequency, the impedance appearing across the terminals of a hybrid stub may be calculated by summing the capacitive reactance of the capacitor with the short circuit reactance of the line segment. While the reactance of the capacitor will decrease inversely proportional to the frequency, the reactance of the line segment will increase with frequency until the line is $\lambda/4$ at the operating frequency, corresponding to anti-resonance, or a very high resistance. By terminating a transmission line segment of proper length with a high Q capacitor, both virtual grounds and virtual open circuits may be impressed on any desired point. In preferred embodiments, transmission line segments are constructed from low loss line, and terminating capacitors are high Q capacitors. Variable capacitors are often used as they allow for fine adjustment of virtual ground and virtual open circuit locations.

Though this design may be applied to most $^1H/X$ nuclear combinations, it will be useful for users to contemplate the behavior of the hybrid notch filters and hybrid termination stubs in the example of a $^1H/^{13}C$ resonator design. The explanation to follow applies also to the following dual nuclear combinations: $^1H/^{23}Na$, $^1H/^{129}Xe$, $^1H/^3He$, and $^1H/^{31}P$.

In the $^1H/^{13}C$ example, the $^{13}C$ notch filter is formed by terminating a section of transmission line of electrical length $\lambda/4$ at $\omega^1H$ ($^1H$ nuclear frequency) with capacitor $C_{N13}$, such that a very low resistive impedance (short circuit) appears across the opposite end of the line section at frequency $\omega^{13}C$. At this frequency, the capacitive reactance of the capacitor is equal in magnitude but opposite in sign to the reactance of a short circuited length of transmission line of the same length, also at $\omega^{13}C$. The length of the $^{13}C$ notch filter line segment is about $\lambda/16$ at $\omega^{13}C$, and its associated short circuit reactance is readily canceled by $C_{N13}$, a capacitor of modest value.

At this point, it is illustrative to consider the behavior of the same hybrid notch filter at $\omega^1H$. At this frequency, the already small reactance of capacitor $C_{N13}$ is ¼ of its previous value, so $C_{N13}$ readily passes RF current at $\omega^1H$. In contrast, the impedance of the short circuit line segment at $\omega^1H$ is very high and resistive, for inversion of a short circuited $\lambda/4$ line transforms a short circuit to an open circuit.

In contrast, the $^1H$ notch filter is constructed from a section of line slightly less than $\lambda/4$, because it is desirable to set the short circuit with a termination capacitor, as done with the X notch filter. In practice, capacitors of less than 0.4 pF or so become problematic, so a slightly shorter line length is chosen such that the line reactance at $\omega^1H$ may be conveniently canceled by a high Q VHF/UHF capacitor. At frequency $\omega^{13}C$, the small capacitor has a reactance in the range of 5,000 to 11,000 ohms or so, while the reactance of the short line segment is quite small, since the line segment is less than $\lambda/16$ at $\omega^{13}C$.

Generally, X notch filters are constructed from line sections $\lambda/4$ in length at $\omega^1H$ and terminated with some capacitor $C_{NX}$ whose value is chosen to cancel short circuit line reactance at $\omega X$. In contrast, $^1H$ filters are constructed from a segment slightly shorter than $\lambda/4$ at $\omega^1H$ for reasons discussed in the example above.

Figure 1A:
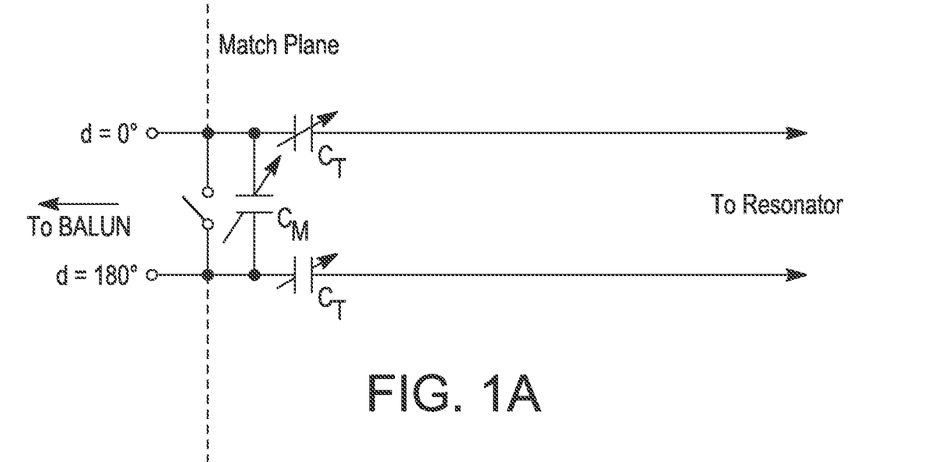
FIG. 1A is a first schematic diagram of a hybrid notch filter accordance to the disclosure.
Figure 1B:
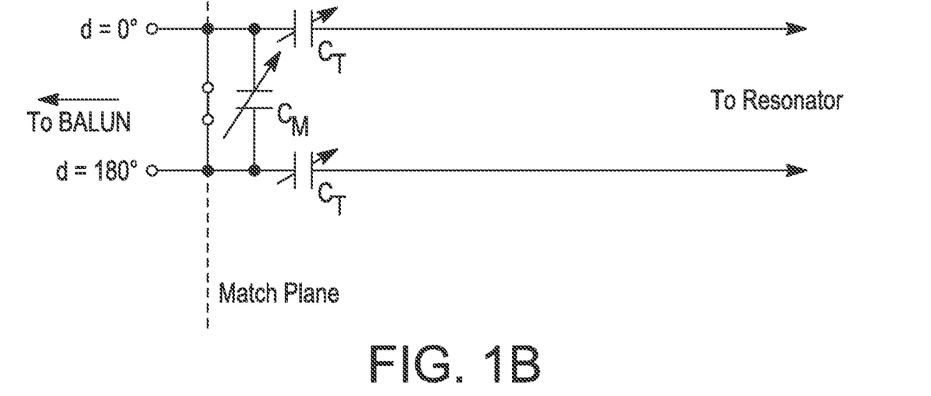
FIG. 1B is a second schematic diagram of a hybrid notch filter accordance to the disclosure.

A conceptual schematic for notch filter action in augmented tune/match circuits is shown in FIG. 1. In FIG. 1A, the hybrid notch filter acts as an open switch at operational frequency ($^1H$ or X) of the balanced tune/match circuit. In FIG. 1B, the hybrid notch filter acts as a closed switch or short circuit at the frequency to be rejected at the match plane. at operational frequency ($^1H$ or X) of the balanced tune/match circuit. $^1H$ hybrid notch rejects $^1H$ frequency and X hybrid notch rejects X frequency. $^1H$ notch is bonded to X tune/match and X notch is bonded to $^1H$ tune/match.

Figure 2:
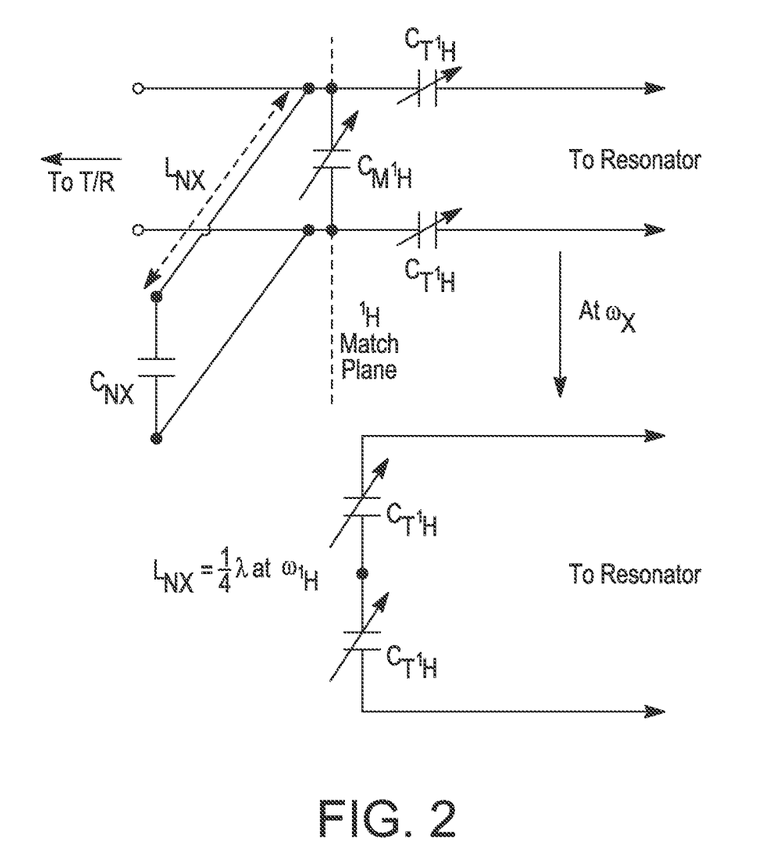
FIG. 2 is a schematic diagram illustrating a $^1$H tune/match circuit.

FIG. 2 shows the effective change in a tune/match circuit when the notch filter applies a short across the match capacitor of the tune/match circuit. The $^1H$ tune/match circuit is transformed to a capacitance line termination at X nucleus frequency $\omega x$. This is effected by the X hybrid notch filter formed by terminating line section $L_{NX}$ with capacitor $C_{NX}$. At the $^1H$ frequency, this notch filter behaves like an open circuit.

Figure 3:
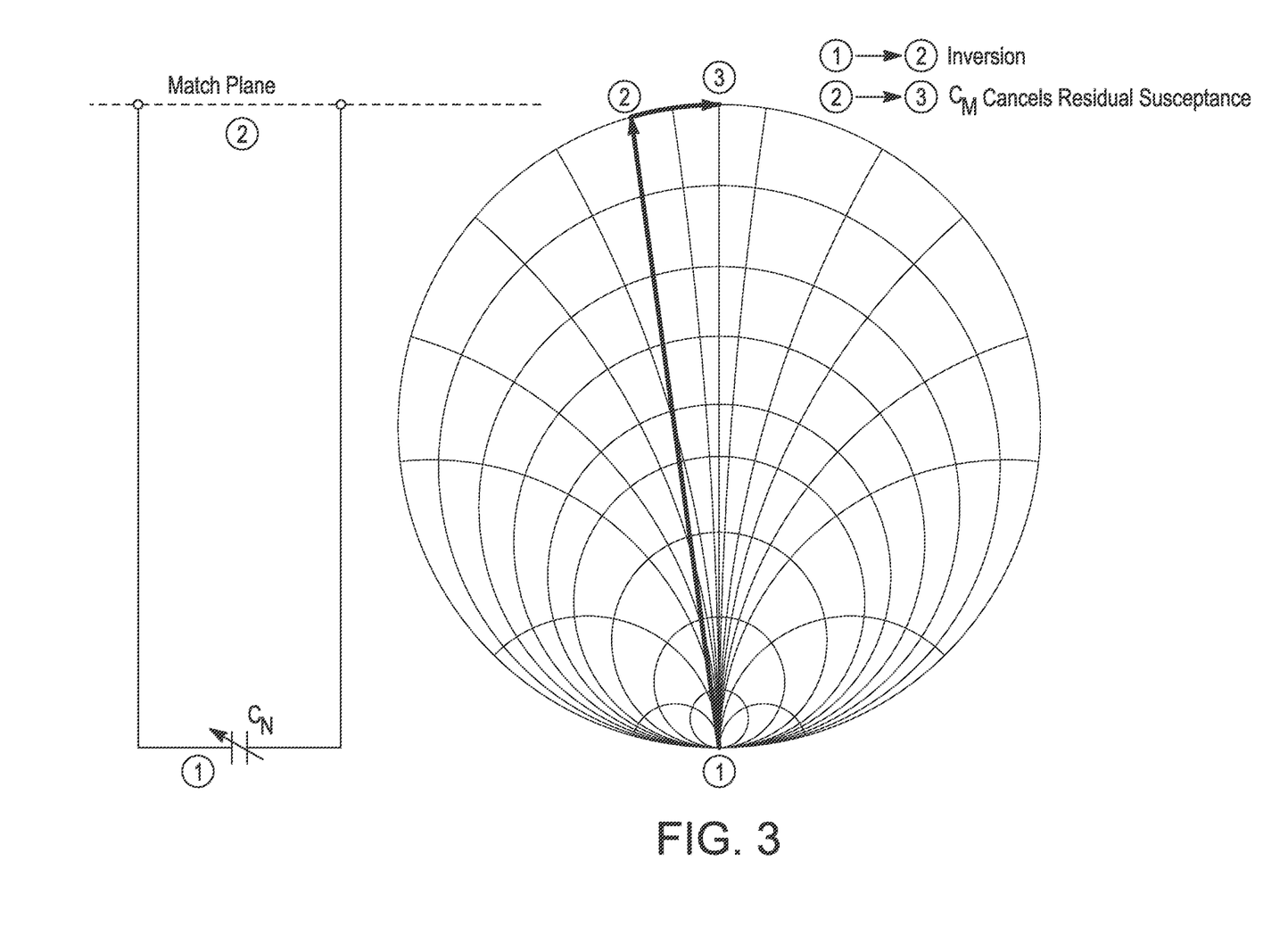
FIG. 3 is an admittance Smith chart of the hybrid notch filter of FIG. 1A at the pass frequency.
Figure 4:
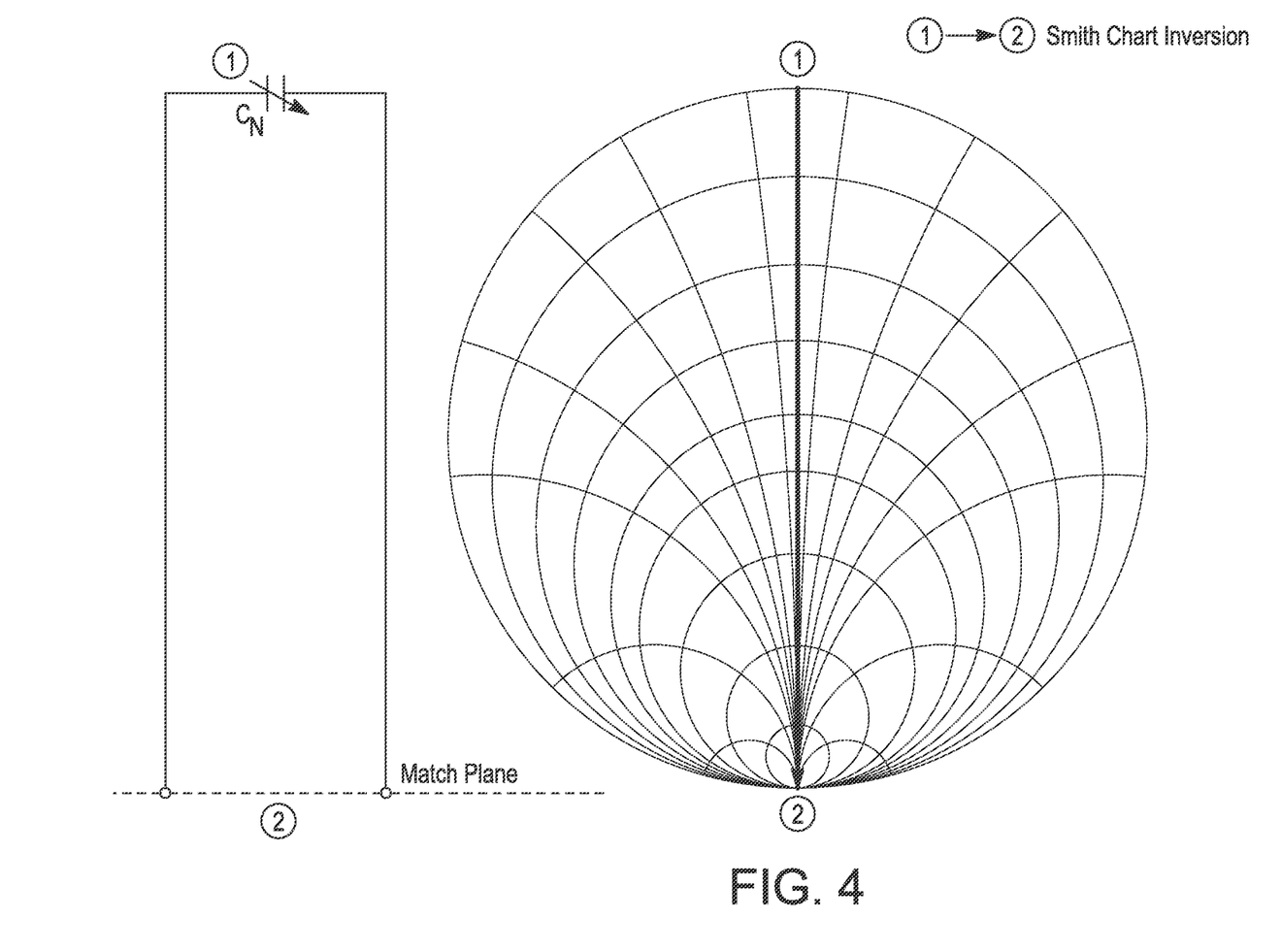
FIG. 4 is an admittance Smith chart of the hybrid notch filter of FIG. 1B at the reject frequency.

Relevant conceptual admittance Smith chart trajectories are shown in FIGS. 3 and 4, with FIG. 3 showing the trajectory corresponding to FIG. 1A and FIG. 4 showing the trajectory corresponding to FIG. 1B. In FIG. 3, at the pass frequency, inversion of hybrid notch admittance (point 1→point 2) leaves but a small amount of susceptance (jB) at point 2. The susceptance is canceled by adjustment of $C_M$ on the tune/match circuit, thereby matching the line shown at point 3. Point 3 is a small conductance, or large resistance in shunt with the feed line. Thus, in FIG. 3 the notch filter puts a low admittance (high impedance) across the match capacitor. Adjustment of $C_M$ cancels the small susceptance of this admittance, leaving only a small conductance or large, pure resistance shunted across $C_M$, resulting in virtually no perturbation of line match, and inserting a negligible line loss. In practical terms, this means shunting a 50 ohm matched line with a pure resistance on the order of 10,000 ohms or more. This introduces virtually no additional load on the line.

In FIG. 4, the conceptual admittance Smith Chart trajectory for notching (short circuit across $C_M$) is shown. At the reject frequency, inversion of hybrid notch (point 1→point 2) produces a large pure conductance at point 2 or short circuit across the feed line. This results in the reflection of almost all RF energy back towards the resonator at the notch frequency.

The overall operation of a complete, dual nuclear resonator according to the disclosure is now described with primary reference to FIGS. 5 and 6 for a surface coil and FIGS. 7 and 8 for a volume coil. The behavior of hybrid transmission lines at different frequencies should be kept in mind with respect to this description.

As desired in preferred embodiments, a $^1$H balanced tune/match circuit is formed by three capacitors 3, 4. The tune/match circuit is connected to a resonator loop (surface coil, FIGS. 5 and 6), or resonator conjugate pair (volume coil driven pair, FIG. 7) by a length of transmission line 5 of some electrical length from virtual ground (V.G.) point. Both $^1$H and X are resonant at the V.G. points. For the $^1$H circuit, this length is conveniently chosen to be around 0.12 to 0.08 wavelength at $\omega^1$H. The tune/match circuit is fed by a high performance current balun 19 (balun 20 is the X current balun) via balanced, shielded lines 17, 18 in preferred embodiments. The balun may be a ferrite bead balun or a sleeve balun. Balun establishes two RF currents of equal magnitude with 180 degree phase difference. Its use permits establishment of floating virtual ground points in the coil, and also eliminates stray RF currents on coaxial cable shields. The tune/match circuit is shunted across $^1$H match capacitor 3 by a X notch filter formed from transmission line segment 2 and capacitor $C_{NX}$ 1. At frequency $\omega^1$H, the tune/match circuit transforms the loaded coil (i.e., a coil with a specimen in the active region) impedance to 50 ohms. Capacitors 4 transform the complex load admittance to the unit conductance circle on admittance Smith Chart. At that point, capacitor 3 is adjusted until load susceptance, capacitor 3 susceptance, and X notch filter susceptance all sum to zero at the match plane. By definition, the line is then matched.

At $\omega$X, the $^1$H tune/match circuit is transformed into a circuit equivalent to placing capacitors 4 in series, while eliminating $C_M$ 3 from the circuit. Thus, the tune/match circuit (formed by capacitors 3, 4) augmented by X notch filter (formed from transmission line segment 2 and capacitor $C_{NX}$ 1) efficiently reflects nearly all RF energy at frequency $\omega$X back towards the active area of the resonator, thereby ensuring that $^1$H tune/match port is well isolated from X port.

Virtual grounds V.G., or shorts (high current points) are established in the arms 12 of surface coil on substrate 11 at frequency $\omega^1$H by action of $^1$H termination element, which is composed of transmission line segment 15 and termination capacitor $C_{1H}$ 16, with length of line segment 15 slightly less that $\lambda$/4 at $\omega^1$H as measured from capacitor 16 to virtual ground point V.G. in the arms 12 of the surface coil.

As with the $^1$H tune/match circuit, the X tune/match circuit is fed by a high performance current balun 20, and formed by capacitors 8, 9, and shunted across capacitor $C_{Mx}$ 8 by $^1$H notch filter formed by line segment 7 and capacitor 6. The X tune/match circuit is placed $\lambda$/4 at $\omega^1$H from x virtual ground point 12. This distance is less than $\lambda$/4 at $\omega$X. As before, X tune/match circuit (formed by capacitors 8, 9) transforms complex load admittance of loaded X coil impedance to 50 ohms. Capacitors 9 transform the complex load admittance to a point on the unit conductance circle of the admittance Smith Chart at frequency $\omega$X. At that point, the X match capacitor 8 is adjusted until load susceptance, X match capacitor susceptance, and $^1$H hybrid notch filter susceptance all sum to zero at the X match plane. The line between X tune/match circuit (formed by capacitors 8, 9) and X current balun 20 is then matched by definition, as was the case with $^1$H tune/match circuit.

At $\omega^1$H, the X tune/match circuit (formed by capacitors 8, 9) is transformed into a circuit equivalent to placing capacitors 9 in series and eliminating capacitor 8. At $\omega^1$H, the transmission line segment 10, terminated on one end by capacitors 9 in series, establishes a very large resistive impedance across the coil loop 12. The x termination element, composed of capacitor 14 and line segment 13, with segment 13 being $\lambda$/4 long at $\omega^1$H, also establishes a large, resistive impedance at $\omega^1$H. Both of these resistors are in series, because termination element 13, 14 and the X augmented/tune match circuit (capacitors 8, 9 in conjunction with line segment 7 and capacitor 6) are effectively in series. This poises no problem for operation of the $^1$H resonator, because $^1$H resonance (virtual ground) is established by $^1$H termination element 15, 16 which is connected in shunt with the X augmented tune/match circuit (capacitors 8, 9 in conjunction with line segment 7 and capacitor 6), and also with X termination element 13, 14. Simple circuit theory shows that a small resistive impedance, or near short, remains a near short when shunted by a large resistance, no matter how large. Thus, $^1$H tune/match and $^1$H termination elements act in concert to resonate the coil on $^1$H and transform the loaded coil impedance to 50 ohms, as desired. Thus, $^1$H circuitry acts as though no X circuitry were present.

At $\omega$X, the augmented $^1$H tune/match circuit (capacitors 3, 4 in conjunction with augmented transmission line segment 2 and capacitor $C_{NX}$ 1) is transformed into the equivalent of a capacitive termination, with capacitors 4 in series, and capacitor 3 removed. At $\omega$X, the augmented $^1$H circuit and its offset line 5 set up a large capacitive reactance (several thousand ohms, for example) at coil arms 12. In a similar manner, $^1$H termination element 15, 16 sets up an even larger capacitive reactance. The end result is a capacitive reactance of around 7,000 ohms (nominal) or more, as both $^1$H augmented tune/match circuit (capacitors 3, 4 in conjunction with augmented transmission line segment 2 and capacitor $C_{NX}$ 1) and $^1$H termination element 15, 16 are effectively in series at $\omega$X. However, both are in shunt with the X augmented tune/match circuit and the X termination element. A large capacitive reactance is essentially "swamped" by a very small resistive impedance, or near short. Thus, X tune/match and X termination elements act in concert to resonate the coil at $\omega$X and transform the loaded coil impedance to 50 ohms at $\omega$X, as desired. Thus, $^1$H circuitry is transparent to X circuitry.

With particular reference to the volume coil shown in FIGS. 7 and 8, one of the driven conjugate pair of the volume coil is shown in FIG. 7. The other would be oriented 90° with respect to the one shown in FIG. 7. FIG. 8 shows a cross section through a passive conjugate pair in a volume coil. The conjugate pair may be terminated on balanced fashion as shown, or in single ended fashion, with each individual element terminated on each end by capacitors 2×$C_x$ and 2×$C^1H$, each capacitor bonded to a ground plane at shield potential. $^1H$ and X capacitors are adjusted to give V.G. at the same points on each conductor for both nuclei.

Preferred embodiments of the resonator and its sub-assemblies and ancillary hardware are now described.

Hybrid notch filters and hybrid termination elements can be constructed from low loss coaxial cable and high q capacitors, usually variable. In the preferred embodiment, hybrid notch filters and hybrid termination elements are constructed from low loss stripline or microstripline transmission line, with the line constructed on low loss substrate such as Rogers Duroid or Rexolite 1422. Conductive track such line should be at least 5 skin depths deep at the X nucleus (lowest) frequency. In the preferred embodiment, well known variants of stripline or microstripline such as meander line and fin line may be used in certain situations. Meander line saves space, while the use of fin line may help reduce dielectric loss at high frequencies, such as 200 MHz or higher. In the preferred embodiment, tune/match circuits, whether balanced capacitive L circuits, or pairs of single ended L circuits, can be feed from high performance current baluns, either ferrite bead ("W2DU balun") or sleeve baluns. The Baluns should have a common mode current resistance of 5,000 to 6,000 ohms or more. Current balance should be within 1% or better, with phase difference of balun output currents within 1 degree of 180 degrees. In the preferred embodiment, shielded, balanced lines constructed from matched lengths of coaxial cable interconnect balun and augmented tune/match circuits. Cables should be integral multiples of ½ wave at the operating frequency of tune/match circuit.

In the special case of $^1H/^3He$ resonators, the hybrid notch filters, and possible the termination elements should be constructed from high Q helical resonators. Since the frequency spacing is small for this particular nuclear pair, it is desirable for the slope of notch filter curve (dV/dω) to be high, which is the case for high Q helical resonators, for Z helix is usually in the range of 800 to 1500 ohms. This allows the filter to return from notch to base in a span of about 9 or 10 MHz. In preferred embodiments, helical resonators will be wound on a low loss substrate, such as air or Rexolite 1422, and enveloped in a highly conductive shield can. Helical resonators may be bonded to tune/match circuits just as hybrid notch filters are so bonded.

In preferred embodiments, either surface coils or volume coils may be fabricated. A plurality of surface coils may serve as a parallel transmit/receive array for accelerated imaging methods such as SMASH (SiMultaneous Acquisition of Spatial Harmonics) or SENSE (SENSitivity Encoding). Surface coils may be flat or conformal in shape.

In preferred embodiments, volume coils are driven with 4 point drive (quadrature), while the other elements are passive, and will couple to other elements by induction. In yet another preferred environment, all elements are phased by DDS transmitter chips, with each conjugate pair of elements driven off a current balun.

In preferred embodiments, arrays of surface coils are controlled and driven off multi-channel DDS transmitters, with each channel assigned a current balun.

Exemplary Example 1

Summary:

In this non-limiting example, a dual nuclear transmission line resonator design according to the disclosure which may be applied to both surface coils and volume coils is presented. The active elements of the resonator are resonant on both $^1H$ and X. No wave trap is used in the active elements, which are essentially "clean" transmission line elements. Efficiency is very high on both $^1H$ and X, and port-to-port isolation is excellent. In this example, a small $^1H/^{13}C$ surface coil is described.

Methods:

A single loop transmission line resonator was constructed from copper clad Rexolite 1422. The loop was designed for 4.7T. This loop is essentially a "swelling" in a balanced transmission line, with an inner diameter of 2 cm. Termination elements were fabricated from equal lengths of HF-290 coaxial line, with ends terminated by variable piston capacitors. The piston capacitors were meshed to give resonance in the middle of the loop on both $^1H$ and $^{13}C$. Balanced capacitive L tune/match circuits were used to match the loop to 50 ohms on both nuclei. Each L was augmented with a complementary nucleus hybrid resonator set to within about 20 KHz of target frequency and connected to a high performance ferrite bead current balun. Scattering parameters ($S_{11}$ and $S_{21}$) measurements were performed on a vector network analyzer (VNA), and 90 degree flips were measured on a Varian 4.7T console. Loop resonance and hybrid resonator adjustments were made using a grid dip meter augmented with a digital frequency counter.

Figure 9:
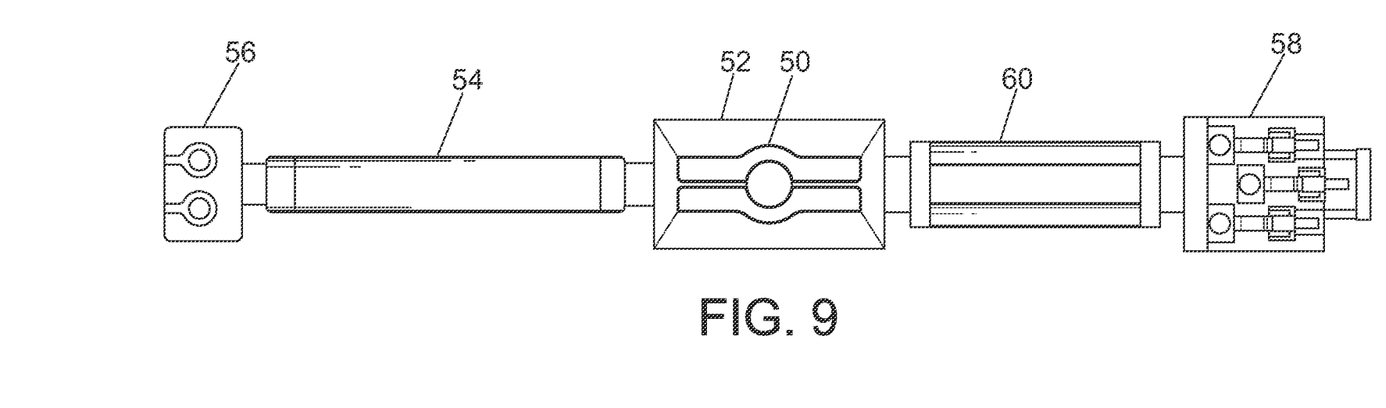
FIG. 9 shows a loop coil and tune/match circuit according to an embodiment of the disclosure.
Figure 10:
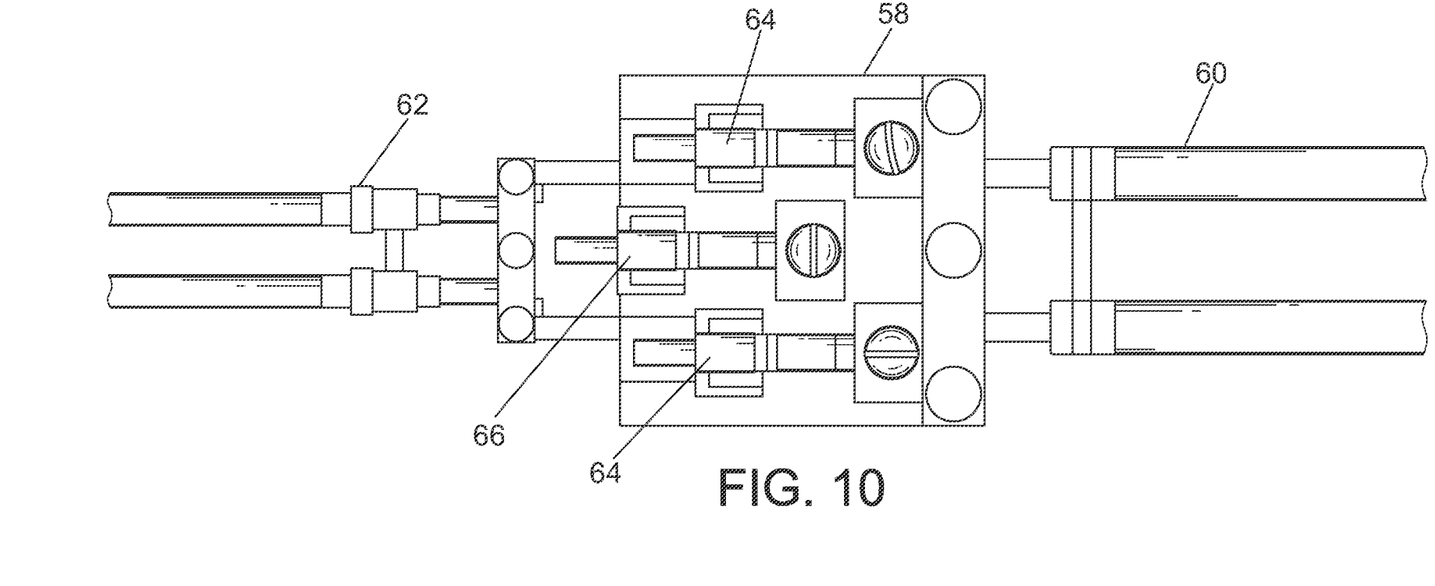
FIG. 10 shows the tune/match circuit of FIG. 9.

FIG. 9 shows surface coil loop 50 mounted on substrate 52 used in this exemplary example. A transmission line 54 with a capacitor 56 (transmission line 54 and capacitor 56 forming the termination stub) connects to one end of surface coil loop 50 and a tune/match circuit 58 connects to the other end of surface coil loop 50 via offset line 60. In FIG. 9, only one nucleus is shown for clarity. As seen in FIG. 10, line portion 62 of a notch filter (capacitor not shown) is connected to tune/match circuit 58. FIG. 10 also shows $C_T$ 64 and $C_M$ 66 of tune/match circuit 54.

Figure 11A:
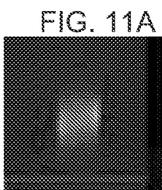
FIG. 11 shows $^1$H spin-echo (SE) images both with $^{13}$C resonator and without $^{13}$C resonator.
Figure 11B:
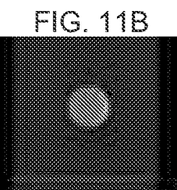
Figure 11C:
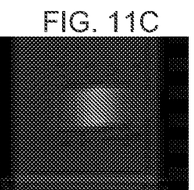
Figure 11D:
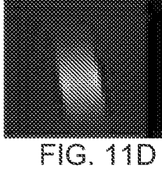
Figure 11E:
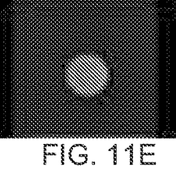
Figure 11F:
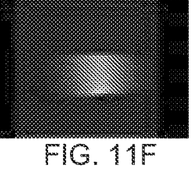

Results:

Good Q was demonstrated on both $^1H$ and $^{13}C$, with −55 dB and −49 dB, respectively, on VNA $S_{11}$ measurements. $S_{21}$ measurements showed −63 dB isolation for $^{13}C \rightarrow {}^1H$, and −45 dB $^1H \rightarrow {}^{13}C$. The low insertion loss of the tune/match augmentation resonators was verified by measuring virtually equal $^1H$ 90 degree flip angle powers with the $^{13}C$ augmentation resonator in circuit and out of circuit. This is shown in FIGS. 11A-11F with $^{13}C$ resonator (FIGS. 11A-C) and without $^{13}C$ resonator (FIGS. 11D-F).

Conclusion:

Careful design and placement of hybrid termination elements and hybrid augmentation resonators leads to the realization of a dual nuclear coil with high efficiency on both $^1H$ and X. This design sidesteps many of the problems inherent in other dual nuclear designs.

REFERENCES

1) Erickson M G, et al. TEM Transmission Line Coil . . . MRM 2007 October 58(4) 800-7.
2) Electronic Applications of the Smith Chart P H Smith, 2nd Edition 1995.

3) Vaughan J T, et al. High frequency volume coils . . . MRM 1994 32 Feb. 6, 2018

Exemplary Example 2

Method:

The dual nuclear transmission line resonator of Exemplary Example 1 was also used for Exemplary Example 2.

Figure 12:
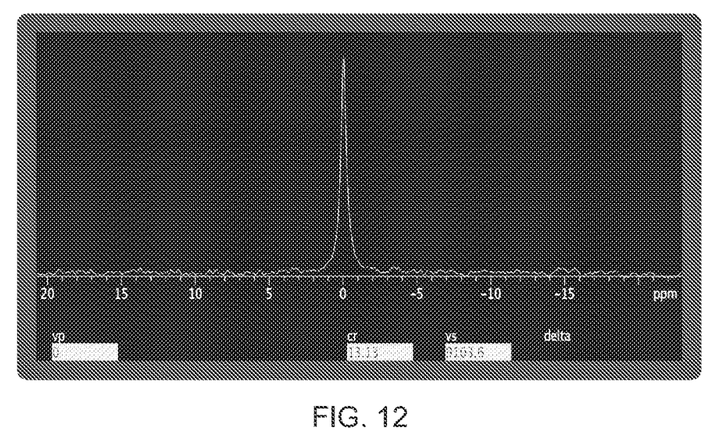
FIG. 12 shows the obtained $^{13}$C spectrum of $^{13}$C urea in ddH$_2$O using a dual nuclear transmission line resonator according to the disclosure.
Figure 13:
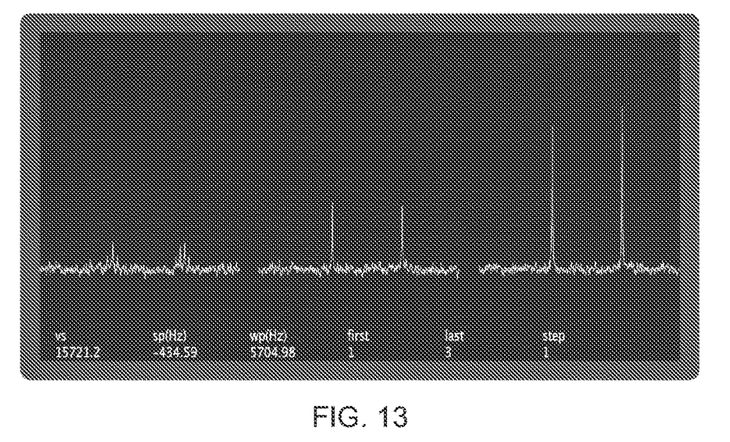
FIG. 13 shows the obtained $^{13}$C spectra of natural abundance ethanol using a dual nuclear transmission line resonator according to the disclosure.

Results:

Unloaded Q was measured for both $^1$H and $^{13}$C by measuring the derivative of the $S_{11}$ curve on either side of resonance. Q was 245 for $^1$H and 196 for $^{13}$C. Next, the coil was loaded with a $^{13}$C urea phantom. After shimming on $^1$H, the $^{13}$C spectrum in FIG. 12 was obtained. Using the same $^{13}$C urea phantom, isolation measurements under load were made. These are shown in FIGS. 13 and 14. $^1$H isolation from the $^{13}$C port was −37 dB, and $^{13}$C isolation from the $^1$H port was −62 dB. FIG. 15 shows $^{13}$C spectra of natural abundance ethanol: on the left, the $^1$H decoupler was off; in the center, $^1$H decoupler was on; and on the right, NOE enhanced decoupling. No retuning or repositioning was required for the acquisition of these spectra. At all times, both the $^1$H coil and the $^{13}$C coil tuned and matched smoothly, with no "cross talk" between the two. In operation, one need only obtain shim on $^1$H, then proceed to X nucleus work.

Conclusion:

An experimental dual nuclear transmission line resonator was successfully constructed and tested. The design side steps many of the problems inherent in conventional dual nuclear designs. No LC trap is used, and the coil has essentially the same spatial profile on both nuclei. This resonator could be used in real time, simultaneous $^1$H/X T/R operation. The resonator is not difficult to fabricate, and lends itself to volume coils and array designs.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

What is claimed is:

1. A dual nuclear MR transmission line resonator, comprising active elements coupled to tune/match circuits configured to match resonance of the active elements to a T/R console on both $^1$H and X of $^1$H/X pairs simultaneously, wherein X is $^{31}$P, $^{23}$Na, $^{13}$C, $^3$He, or $^{129}$Xe, wherein a hybrid notch filter tuned to notch or short circuit at a frequency of a companion nucleus is shunted across each of the tune/match circuits on a side opposite the coupling to the active elements.

2. The dual nuclear MR transmission line resonator of claim 1, wherein the active elements comprise conductive elements in a utility region of the dual nuclear MR transmission line resonator that are simultaneously resonated on both $^1$H and X with high efficiency.

3. The dual nuclear MR transmission line resonator of claim 1, where the dual nuclear MR transmission line resonator has virtually identical spatial distributions on both $^1$H and X frequencies.

4. The dual nuclear MR transmission line resonator of claim 1, wherein the active elements act as a T/R coil for both $^1$H and X independently of each other.

5. A resonator, comprising:
a coil coupled to tune/match circuits, wherein a hybrid notch filter tuned to notch or short circuit at a frequency of a companion nucleus is shunted across each of the tune/match circuits on a side opposite the coupling to the coil, where a $B_0$ static field of a MR magnet is fine adjusted using a $^1$H frequency of a $^1$H/X pair simultaneously generated by the coil, thereby automatically adjusting $B^0$ for both $^1$H and of the $^1$H/X pair for imaging or spectroscopy due to perfect spatial co-registration of the coil on both 1H and X.

6. A method, comprising:
simultaneously resonating conductive loops of a surface coil or conductive elements of a volume coil on both $^1$H and X with a plurality of hybrid transmission line termination elements, the conductive loops of the surface coil or the conductive elements of the volume coil coupled to tune/match circuits, wherein a hybrid notch filter tuned to notch or short circuit at a frequency of a companion nucleus is shunted across each of the tune/match circuits on a side opposite the coupling to the conductive loops or the conductive elements, said plurality of hybrid transmission line termination elements bonded to the conductive loops or conductive elements in shunt with respect to one another.

7. An augmented MR tune/match circuit, comprising:
a capacitive L circuit comprising capacitors coupled in an L-configuration, with said capacitive L circuit shunted at a match plane of a T/R operating frequency by a hybrid notch filter tuned to notch or short circuit at a frequency of a companion nucleus, the hybrid notch filter shunted across the capacitive L circuit on a side configured to couple to T/R circuitry that provides the T/R operating frequency.

8. The augmented MR tune/match circuit of claim 7, wherein the hybrid notch filter is constructed from a hybrid transmission line circuit or a helical resonator notching at the companion nucleus frequency.

9. The augmented MR tune/match circuit of claim 8, wherein the augmented MR tune/match circuit acts as a normal tune/match port at the T/R operating frequency, while acting as a virtual short circuit termination at the frequency of the companion nucleus.

10. The augmented MR tune/match circuit of claim 7, wherein a plurality of resonators are coupled to a plurality of the augmented MR tune/match circuits, the plurality of resonators configured in arrays for an accelerated imaging modality.

11. The augmented MR tune/match circuit of claim 10 wherein the accelerated imaging modality is SMASH (SiMultaneous Acquisition of Spatial Harmonics) or SENSE (SENSitivity Encoding).

12. The augmented MR tune/match circuit of claim 7, wherein one or a plurality of resonators is run off analog T/R circuitry, or is used in conjunction with at least one of multi-channel DDS controlled transmitters and multi-channel digital receivers.

13. The augmented MR tune/match circuit of claim 12, wherein the analog T/R circuitry is quadrature hybrid circuitry.

14. The augmented MR tune/match circuit of claim 7, wherein the capacitive L circuit is a balanced capacitive L circuit comprising a variable tuning capacitor connected in each of a pair of transmission lines connected to a resonator and a variable matching capacitor connected between the pair of transmission lines.

15. The augmented MR tune/match circuit of claim 7, wherein the capacitive L circuit comprises a pair of single-ended capacitive L circuits comprising a variable tuning capacitor connected in each of a pair of transmission lines connected to a resonator and variable matching capacitors connected to each of the pair of transmission lines and a ground plane.

* * * * *